United States Patent [19]
Helton et al.

[11] Patent Number: 5,661,184
[45] Date of Patent: Aug. 26, 1997

[54] PSYCHIATRIC AGENTS

[75] Inventors: David R. Helton; Mary Jeanne Kallman, both of Greenfield; James A. Monn; Darryle D. Schoepp, both of Indianapolis; Joseph P. Tizzano, New Palestine, all of Ind.

[73] Assignee: Eli Lilly and Company, Indianapolis, Ind.

[21] Appl. No.: 496,642

[22] Filed: Jun. 29, 1995

Related U.S. Application Data

[63] Continuation-in-part of Ser. No. 337,349, Nov. 10, 1994, abandoned, which is a continuation-in-part of Ser. No. 289,957, Aug. 12, 1994, abandoned.

[51] Int. Cl.$^6$ .................................................. A61K 31/19
[52] U.S. Cl. .................... 514/574; 514/810; 514/811; 514/812; 514/813
[58] Field of Search ................................ 514/574, 810, 514/811, 812, 813

[56] References Cited

FOREIGN PATENT DOCUMENTS

WO95/15940  6/1995  WIPO.

OTHER PUBLICATIONS

Koch, "Microinjections . . . (trans–ACPD) . . . Amydala . . . Rats", Brain Research, vol. 629, 176–179 1993.

Y. Nakagawa et al., "(2S,3S,4S)α–(Carboxycyclopropyl)–glycine is a novel agonist of metabotropic glutamate receptors," European J. Pharmacology, 184, 205–206 (1990).

Y. Hayashi et al., "Agonist analysis of 2–(carboxycyclopropyl)glycine isomers for cloned metabotropic glutamate receptor subtypes expressed in Chinese hamster ovary cells," Br. J. Pharmacol., 107, 539–543 (1992).

H. Shinozaki and M. Ishida, "Recent Advances in the Study of Glutamate Receptor Agonists," Asia Pacific J. of Pharmacol., 6, 293–316 (1991).

Canadian Journal of Pharmacology, XIIth International Congress of Pharmacology Abstracts, vol. 72, Supplement 1, issued 24 Jul. 1994, M.E. Fundytus, et al., "Acute ICV Injection of the Metabotropic Glutamate Receptor Agonists trans–ACPD Attenuates Morphine Withdrawal in Rats", p. 349, col. 2, Abstract No. P13.5.18.

Neuroscience Letters, vol. 162, issued 1993, abstract, Tizzanno et al, "Intracerebral 1S,3R–1–Aminocyclopentane–1, 3–Dicarboxylic Acid (1S,3R–ACPD) Produces Limbic Seizures that are not Blocked by Ionotropic Glutamate Receptor Antagonists", pp. 12–16.

F. Nicoletti et al., "(1$_S$, 1'$_R$, 2'$_R$, 3'$_R$)–2–(2,3–Dicarboxycyclopropyl)glycine enhances quisqualate–stimulated inositol phospholipid hydrolysis in hippocampal slices," Eur. J. Pharmacol.–Molecular Pharmacol. Section, 245, 297–298 (1993).

M. Ishida et al., "A potent metabotropic glutamate receptor agonist: electrophysiological actions of a conformationally restricted glutamate analogue in the rat spinal cord and Xenopus oocytes," Brain Res., 537, 311–314 (1990).

M. Ishida et al., "A novel metabotropic glutamate receptor agonist: marked depression of monosynaptic excitation in the newborn rat isolated spinal cord," Br. J. Pharmacol., vol. 109, 1169–1177 (Aug. 1993), abstract.

V. Bruno et al., "Protective effect of the metabotropic glutamate receptor agonist, DCG–IV, against excitotoxic neuronal death," Eur. J. Pharmacol., 256, 109–112 (1994).

H, Kaba et al., "Induction of an Olfactory Memory by the Activation of a Metabotropic Glutamate Receptor," Science, 265, 262–264 (Jul. 8, 1994).

D.E. Jane et al., "Actions of two new antagonists showing selectively for different sub–types of metabotropic glutamate receptor in the neonatal rat spinal cord," Br. J. Pharmacol., 112, 809–816 (1994).

F. Nicoletti et al., "Effect of Metabotropic Glutamate Receptor Agonists in Excitotoxic or Apoptotic Neuronal Degeneration," Neuropschychopharmacology, 10 (3S), 623S (1994) May.

M. Mortensen et al., "The Effect of Lorazepam Tolerance and Withdrawal on Metabotropic Glutamate Receptor Function" Journal of Pharmacology and Experimental Therapeutics 274(1), (Mar. 27, 1995) pp. 155–163.

Alcohol Clin. Exp. Res., vol. 17 (4), S. A. Queen et al., "Dose and Age–Dependent Effects of Prenatal Ethanol Exposure . . . Metabotropic Glutamate Receptor . . . Hydrolysis", 1993, abstract.

Alcohol, vol. 11 (4), T. L. Smith, "Selective Effects of Ethanol Exposure on Metabotropic GlutamateProduces Limbic Seizures . . . Glutamate Receptor and Nucleotide . . . Astrocytes", 1994, abstract.

Molecular and Chemical Neuropathology, vol. 23 (1), P. G. Rhodes et al., "Prenatal Ethanol and Exposure Reduces Phosphoinositide Hydrolysis . . . Cell Cultures":, 1994, abstract.

Primary Examiner—José G. Dees
Assistant Examiner—Rosalynd Williams
Attorney, Agent, or Firm—Martin A. Hay; David E. Boone; James P. Leeds

[57] ABSTRACT

The present invention provides a method of treating substance dependence disorders using an agonist which acts at negatively coupled cAMP–linked metabotropic glutamate receptors.

26 Claims, No Drawings

PSYCHIATRIC AGENTS

This application is a continuation-in-part of application Ser. No. 08/337,349 filed Nov. 10, 1994, now abandoned which is itself a continuation-in-part of application Ser. No. 08/289,957, filed Aug. 12th, 1994, now abandoned.

BACKGROUND OF THE INVENTION

The present invention relates to treatments for substance dependence.

Substance dependence is a major problem, both for individuals suffering from it, and for society at large. At the individual level, the condition is characterized by a need for repeated, and often increasing doses of a substance. At the societal level, the condition is associated, with some substances, with increased levels of crime, including theft and crimes of violence, as sufferers seek to obtain supplies of the substance.

Individuals dependent on a substance find that they have to continue taking the substance, even though it produces harmful effects in them. They may become tolerant to the substance, which means that they need to take greatly increased amounts, for example ten times the amount they originally took, in order to achieve the same effect. Withdrawal of the substance brings about a variety of undesirable behavioral and physiological changes, including craving for the substance, anxiety and irritability.

In the mammalian central nervous system (CNS), the transmission of nerve impulses is controlled by the interaction between a neurotransmitter, that is released by a sending neuron, and a surface receptor on a receiving neuron, causing excitation of this receiving neuron.

L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, emotional states and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The metabotropic glutamate receptors are a highly heterogeneous family of glutamate receptors that are linked to multiple second-messenger pathways. Generally, these receptors function to modulate the presynaptic release of glutamate, and the postsynaptic sensitivity of the neuronal cell to glutamate excitation. The metabotropic glutamate receptors (mGluR) have been pharmacologically divided into two subtypes. One group of receptors is positively coupled to phospholipase C, which causes hydrolysis of cellular phosphoinositides (PI). This first group are termed PI-linked metabotropic glutamate receptors. The second group of receptors is negatively coupled to adenyl cyclase, which prevents the forskolin-stimulated accumulation of cyclic adenosine monophosphate (cAMP). Schoepp and Conn, *Trends Pharmacol. Sci.*, 14, 13 (1993). Receptors within this second group are termed cAMP-linked metabotropic glutamate receptors.

There are many different substances on which individuals may become dependent. These include opiates, benzodiazepines, nicotine, cocaine and ethanol.

Nicotine dependence, which is induced through smoking, affects hundreds of millions of people around the world. For many, it leads to illness and premature death. Stopping smoking (smoking cessation) may evoke a range of symptoms in dependent individuals, including craving, depression, anxiety, difficulty in concentrating and weight gain.

A variety of treatments are available for smoking cessation, including counseling, hypnosis, aversion conditioning, relaxation training, acupuncture, and nicotine replacement therapy. However, in spite of the availability of these treatments, and the widespread knowledge of the harmful side effect of smoking, many smokers fail to give up smoking. There is therefore a need for new treatments for smoking cessation.

Benzodiazepine dependence, such as diazepam dependence, arises through the use of the benzodiazepines as pharmaceuticals to treat other disorders. The dependence-inducing properties of the benzodiazepines limits their therapeutic use. Withdrawal produces symptoms such as anxiety, irritability, insomnia and impaired concentration. There is therefore a need for new treatment for the treatment of benzodiazepine withdrawal.

Animal models for the treatment of nicotine and diazepam withdrawal have been described in Helton et al.; Psychopharmacology (1993), 113:205–210 and Rasmussen et al.; Neuroreport 5, 154–156 (1993). These models can be used to measure the ability of a test compound to inhibit the increased startle response in an animal (rat) following withdrawal of nicotine or diazepam.

It has now been found that a compound which is an agonist that acts selectively at negatively coupled cAMP-linked metabotropic glutamate receptors is capable of reducing startle response in rats following the cessation of chronic nicotine or diazepam exposure. It is believed that this finding portends that any agonist that acts at negatively coupled cAMP-linked metabotropic glutamate receptors will be useful for treating substance withdrawal, and indeed may be useful for providing protection against substance dependence.

SUMMARY OF THE INVENTION

According to one aspect, therefore, the present invention provides a method of protecting a warm blooded mammal from dependence on a substance, which comprises administering to a warm-blooded mammal in need of protection an effective amount of an agonist which acts at negatively coupled cAMP-linked metabotropic glutamate receptors.

DETAILED DESCRIPTION OF THE INVENTION

It has been found that a novel compound which is an agonist that acts selectively at negatively coupled cAMP-linked metabotropic glutamate receptors, (+)-2-aminobicyclo[3.1.0]hexane-2,6-dicarboxylic acid is effective in the rat startle models for nicotine and diazepam withdrawal. Accordingly it is believed that any compound which acts as an agonist at negatively coupled cAMP-linked metabotropic glutamate receptors, especially any agonist which acts selectively, will be useful for the treatment of the withdrawal or cessation of these and other dependence-producing substances. Furthermore, since withdrawal is intimately related to dependence and to tolerance, it is believed that an agonist which acts at negatively coupled cAMP-linked metabotropic glutamate receptors will also be useful for the treatment of substance dependence and tolerance, and indeed generally to protect a warm blooded mammal from dependence on a dependence-producing substance.

The dependence-producing substance may be, for example, an opiate, benzodiazepine, nicotine, cocaine or ethanol.

According to another aspect, the present invention provides a method of treating a warm blooded mammal for drug tolerance, withdrawal or cessation, which comprises administering to a warm blooded mammal in need of treatment an effective amount of an agonist which acts at negatively coupled cAMP-linked metabotropic glutamate receptors.

According to yet another aspect, the present invention provides a method of treating a warm blooded mammal for smoking cessation, which comprises administering to a warm blooded mammal in need of treatment an effective amount of an agonist which acts at negatively coupled cAMP-linked metabotropic glutamate receptors.

The particular dose of agonist administered according to this invention will of course be determined by the particular circumstances surrounding the case, including the activity of the particular agonist administered, the route of administration, the particular condition being treated, and similar considerations. The agonist can be administered by a variety of routes including oral, rectal, transdermal, subcutaneous, intravenous, intramuscular, or intranasal routes. Alternatively, the agonist may be administered by continuous infusion. A typical daily dose will contain from about 0.001 mg/kg to about 100 mg/kg of the agonist. Preferably, daily doses will be about 0.05 mg/kg to about 50 mg/kg, more preferably from about 0.1 mg/kg to about 20 mg/kg.

According to preferred aspect, the present invention provides a method of protecting a warm-blooded mammal from dependence on a dependence-producing pharmaceutical, for example, a benzodiazepine such as diazepam. In this method, the agonist may be administered before said pharmaceutical is first administered, after said pharmaceutical has been administered or after said pharmaceutical has been withdrawn, or it may be co-administered with said pharmaceutical.

Agonists which act at negatively coupled cAMP-linked metabotropic glutamate receptors may be identified using the following experiment. Firstly, the affinity of a test compound for metabotropic glutamate receptors may be demonstrated by the selective displacement of (1S, 3R)-1-aminocyclopentane-1,3-dicarboxylic acid-sensitive [$^3$H] glutamate binding to rat brain cell membranes. The binding of [$^3$H]glutamate ([$^3$H]Glu) is conducted with crude membranes of rat forebrain as described by Schoepp and True. Schoepp and True, *Neuroscience Lett.*, 145, 100–104 (1992); Wright, McDonald, and Schoepp, *J. Neurochem.*, 63, 938–945 (1994). The affinity of a test compound for the receptor may be expressed as the concentration of the test compound that inhibits 50% binding (IC$_{50}$), or the percent displacement of [$^3$H]Glu at a 10 μM or 100 μM concentration of the formula I compound. In this test, the IC$_{50}$ for (+)-2-aminobicyclo[3.1.0]hexane-2,6-dicarboxylic acid was found to be 0.18 μM.

The ability of a test compound to act as an agonist at negatively coupled cAMP-linked metabotropic receptors may be measured using the following method. Test compounds are tested for their ability to decrease forskolin-stimulated cAMP formation in the rat hippocampus and the rat cerebral cortex, using the procedures described in Schoepp and Johnson. Schoepp and Johnson, *Neurochem. Int.*, 22, 277–283 (1993). In this test, (+)-2-aminobicyclo [3.1.0]hexane-2,6-dicarboxylic acid was found to give the result shown in Table II below.

TABLE II

| Inhibition of Forskolin-Stimulated cAMP Formation | |
|---|---|
| EC$_{50}$ (μM) | |
| Rat cerebral cortex | .055 ± .017 |
| Rat hippocampus | .036 ± .015 |

The ability of negatively coupled cAMP-linked metabotropic receptor agonists to protect a warm blooded mammal from the effects of drug withdrawal or cessation may be demonstrated using an auditory startle model. In this model, animals are dosed with a drug (nicotine or diazepam), then dosing is discontinued. This cessation of drug dosing elicits an increased startle response to auditory stimuli. Test compounds are then administered to animals to determine whether they are capable of attenuating the increased startle response.

Long Evans rats (200–400 g; Harlan Sprague Dawley, Columbus, Ind.) were individually housed in a controlled environment on a 12 hour light-dark cycle and given free access to food (Purina Rodent Chow) and water. Rats were anesthetized with isoflurane and Alzet osmotic pumps (Alza Corporation) were implanted subcutaneously.

Test compound was dissolved in a vehicle of purified water and neutralized with 5N NaOH to a pH of 7–8 when applicable. Diazepam (Sigma Chemical Company, St. Louis, Mo.) was suspended in a vehicle consisting of 40% PEG 300, 10% EtOH, 2% benzyl alcohol, 1% Tween 80, and 47% purified water. Nicotine (Research Biochemicals Inc., Natick, Mass.) was dissolved in saline. Control animals received the respective vehicle.

Nicotine withdrawal:

Pumps were filled to deliver nicotine (6 mg/kg/day s.c.), diazepam (10 mg/kg/day s.c.), test compound (0,1,3,10 mg/kg s.c.) or vehicle. Twelve days following subcutaneous implantation of pumps, rats were anesthetized with isoflurane and the pumps were removed. During withdrawal (following pump removal), the auditory startle response (peak amplitude, Vmax) of individual rats was recorded using San Diego Instruments startle chambers (San Diego, Calif.). Startle sessions consisted of a 5-minute adaptation period at a background noise level of 70±2 dBA immediately followed by 25 presentations of auditory stimuli (120±2 dBA noise, 50 ms duration) presented at 8-second intervals. Peak startle amplitudes were then averaged for all 25 presentations of stimuli for each session and all data are presented here as overall session means. Auditory startle responding was evaluated daily on withdrawal days 1,2,3,4 or 5. Baseline startle responding was evaluated prior to pump removal on day 12.

Auditory startle responding was significantly increased through the first three days following cessation of chronic nicotine exposure when compared to control rats receiving water. Rats given a replacement dose of nicotine at doses of 0.03 mg/kg, i.p. or higher did not display the same heightened startle response seen for animals with no nicotine replacement. Pretreatment with (+)-2-aminobicyclo[3.1.0]hexane-2,6-dicarboxylic acid produced a dose-dependent blockade of the withdrawal-induced increase in startle responding as well. A significant attenuation of the heightened startle was apparent at 3 mg/kg, p.o. dose of the compound when compared to nicotine controls ($ED_{50}$=0.7 mg/kg i.p.).

Diazepam Withdrawal:

Auditory startle responding was significantly increased through the first four days following cessation of chronic diazepam exposure when compared to control rats receiving vehicle. Replacement doses of 3 and 10 mg/kg, i.p. diazepam did not block the increased startle responding and in some instances further increased reactivity indicating tolerance. Rats which received 30 mg/kg, i.p. diazepam replacement daily 60 minutes before evaluation of startle responding, did not show increased reactivity following diazepam cessation on days 1 through 4 when compared to the diazepam control. Pretreatment with (+)-2-aminobicyclo[3.1.0] hexane-2,6-dicarboxylic acid blocked the expected increase in startle responding which followed cessation of diazepam exposure. Doses of 0.1 and 0.3 mg/kg, p.o. of the compound significantly attenuated enhanced startle when compared to control responding ($ED_{50}$=0.1 mg/kg, p.o.).

(+)-2-Aminobicyclo[3.1.0]hexane-2,6-dicarboxylic acid may be prepared by reacting carbethoxymethyl dimethylsulfonium bromide with 2-cyclopenten-1-one in the presence of a base, such as 1,8-diazabicyclo[5.4.0]undec-7-ene to afford ethyl 2-oxobicyclo[3.1.0]hexane-6-carboxylate. This ester may then be reacted with an aqueous solution of potassium cyanide or sodium cyanide and ammonium carbonate to produce an intermediate hydantoin, (the Bucherer-Bergs reaction), which is then hydrolysed using sodium hydroxide, to afford a diastereomeric mixture of diethyl 2-aminobicyclo[3.1.0]hexane-2,6-dicarboxylates. The desired diastereomer may be obtained by crystallization with oxalic acid. This diastereomer may then be resolved by forming a crystalline salt with (+)-di-p-toluoyl-D-tartaric acid and recovering (−)-diethyl 2-aminobicyclo[3.1.0]hexane-2,6-dicarboxylate- Hydrolysis of this diester using aqueous sodium hydroxide gives (+)-2-aminobicyclo[3.1.0]hexane-2,6-dicarboxylic acid. Alternatively, the ethyl 2-oxobicyclo[3.1.0]hexane-6-carboxylic acid may be hydrolysed using sodium hydroxide to give 2-oxobicyclo[3.1.0]hexane-6-carboxylic acid. This acid may then be resolved by forming a crystalline salt with (S)-1-phenylethylamine and recovering (+)-2-oxobicyclo[3.1.0]hexane-6-carboxylic acid. This acid may then be converted into (+)-2-aminobicyclo[3.1.0]hexane-2,6-dicarboxylic acid by reaction with an aqueous solution of potassium cyanide or sodium cyanide and ammonium carbonate to produce an intermediate hydantoin (the Bucherer-Bergs reaction) followed by hydrolysis of the hydantoin using sodium hydroxide. This procedure may also be modified by performing the resolution step on the hydantoin rather than on the 2-oxobicyclo[3.1.0]hexane-6-carboxylic acid. In this case, (R)-1-phenylethylamine has been found to be a suitable resolving agent.

The agonists are preferably formulated prior to administration in combination with one or more pharmaceutically-acceptable carriers, diluents, or excipients. The pharmaceutical formulations are prepared by known procedures using well-known and readily available ingredients. In making the compositions, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, dermal patch, subcutaneous implant, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, stearic acid, and mineral oil. The formulations can additionally include lubricating agents, wetting agents (surfactants), emulsifying and suspending agents, preserving agents, sweetening agents, or flavoring agents. Compositions may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 200 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

| Formulation 1 Hard gelatin capsules are prepared using the following ingredients: | |
|---|---|
| | Quantity (mg/capsule) |
| 2-Aminobicyclo[3.1.0]hexane-2,6-dicarboxylic Acid | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| 2-Aminobicyclo[3.1.0]hexane-2,6-dicarboxylic Acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| 2-Aminobicyclo[3.1.0]hexane-2,6-dicarboxylic Acid | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| 2-Aminobicyclo[3.1.0]hexane-2,6-dicarboxylic Acid | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg of active ingredient are made as follows:

| 2-Aminobicyclo[3.1.0]hexane-2,6-dicarboxylic Acid | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| 2-Aminobicyclo[3.1.0]hexane-2,6-dicarboxylic Acid | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of active ingredient per 5 ml dose are made as follows:

| 2-Aminobicyclo[3.1.0]hexane-2,6-dicarboxylic Acid | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| 2-Aminobicyclo[3.1.0]hexane-2,6-dicarboxylic Acid | 100 mg |
|---|---|
| Mannitol | 100 mg |
| 5 N Sodium hydroxide | 200 ml |
| Purified water to total | 5 ml |

The following Examples further illustrate methods for their synthesis of (+)-2-aminobicyclo[3.1.0]hexane-2,6-dicarboxylic acid. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use. Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz. Free atom bombardment mass spectroscopy (FABMS) was performed on a VG ZAB-2SE instrument. Field desorption mass spectroscopy (FDMS) was performed using either a VG 70SE or a Varian MAT 731 instrument. Optical rotations were measured with a Perkin-Elmer 241 polarimeter. Chromatographic separation on a Waters Prep 500 LC was generally carried out using a linear gradient of the solvents indicated in the text. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash chromatography was performed as described by Still, et al. Still, Kahn, and Mitra, *J. Org. Chem.*, 43, 2923 (1978). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Gallenkamp hot air bath melting point apparatus or a Büchi melting point apparatus, and are uncorrected. The number in parenthesis after the compound name refers to the compound number.

Preparation 1

Carbethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88°–90° C.

EXAMPLE 1

(1SR,5RS, 6SR) Ethyl 2-Oxobicyclo[3.1.0]hexane-6-carboxylate

A suspension of carbethoxymethyl diethylsulfonium bromide (45.5 g) in toluene (350 mL) was treated with 1,8-diazabicyclo[5.4.0]undec-7-ene (30.2 g). The resulting mixture was stirred at room temperature. After one hour, the reaction mixture was treated with 2-cyclopenten-1-one (19.57 g). After an additional 18 hours, the reaction mixture was added to a 1N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g of the title compound. Melting point: 36°–38° C.

FDMS: m/z=168 (M+).

Analysis calculated for $C_9H_{12}O_3$: C, 64.27; H, 7.19. Found: C, 64.54; H, 7.11.

EXAMPLE 2

(1SR,2RS,5RS,6SR) Diethyl 2-Aminobicyclo[3.1.0] hexane-2,6-dicarboxylate and (1SR,2SR,5RS,6SR) Diethyl 2-Aminobicyclo[3.1.0] hexane-2,6-dicarboxylate A solution of the compound prepared as described in Example 1 (22.81 g) in ethanol (200 mL) was treated with an aqueous solution of potassium cyanide (9.71 g) and ammonium carbonate (21.2 g) in water (200 mL). The resulting mixture was heated to about 50° C. After about 18 hours, the reaction mixture was allowed to cool to room temperature and treated with sodium hydroxide (16.2 g). The resulting mixture was heated to reflux. After about 18 hours, the reaction mixture was allowed to cool to room temperature, then cooled to 0° C. The pH of the cold mixture was adjusted to pH 1 by the addition of concentrated hydrochloric acid. This mixture was concentrated to dryness in vacuo. The residue was dissolved in ethanol, cooled to 0° C., and treated with thionyl chloride (80.6 g). The resulting mixture was heated to reflux. After about 48 hours, the reaction was concentrated to dryness in vacuo. The residue was treated with 1N sodium hydroxide, and the resulting mixture extracted with diethyl ether. The combined ether extracts were dried over potassium carbonate, filtered, and concentrated in vacuo to give 24.6 g of a mixture of the title compounds.

EXAMPLE 3

(1SR,2SR,5RS,6SR) Diethyl 2-Aminobicyclo[3.1.0] hexane-2,6-dicarboxylate

A solution of the compounds prepared as described in Example 2 (20.71 g) in ethyl acetate (200 mL) was treated with a solution of oxalic acid (15.46 g) in ethanol (50 mL). The resulting mixture was stirred at room temperature. After one hour, the reaction mixture was treated with additional ethanol (50 mL). After 18 hours, the mixture was filtered, and the filtrate was evaporated to dryness in vacuo. The residue was treated with 1N sodium hydroxide, and the resulting mixture extracted with diethyl ether. The combined ether extracts were washed with brine, dried over potassium carbonate, filtered, and concentrated in vacuo. The residue was purified by silica-gel chromatography, eluting with methylene chloride: 5% ammonium hydroxide/methanol (97:3), to give 15.41 g of the title compound.

FDMS: m/z=242 (M+H).

Analysis calculated for $C_{12}H_{19}NO_4$: C, 59.74; H, 7.94; N, 5.81. Found: C, 59.78; H, 8.13; N, 5.77.

EXAMPLE 4

(−)-Diethyl 2-Aminobicyclo[3.1.0]hexane-2,6-dicarboxylate

A solution of the racemic mixture of compounds prepared as described in Example 3 (6.56 g) in ethyl acetate (100 mL) was treated with a solution of (+)-di-p-toluoyl-D-tartaric acid (12.0 g) in ethyl acetate (100 mL). After standing overnight at room temperature, the crystalline solid was removed by filtration and dried to give 14.7 g. Additional crystalline solid was obtained by cooling the filtrate to 0° C. The combined crystalline solids were dissolved in hot ethyl acetate, containing enough 2- propanol for complete dissolution. After cooling to 0° C., the crystalline solid was isolated by filtration, to give 2.3 g of a solid having an enantiomeric excess of ≧95%. The freebase form was obtained by partitioning the salt between aqueous sodium bicarbonate and ethyl acetate. The organic phase was separated, dried over potassium carbonate, filtered, and concentrated in vacuo to give 0.77 g of the title compound.

FDMS: m/z=242 (M+H).

Optical rotation: $\alpha_D$=−5.15° (c=1, EtOH).

Analysis calculated for $C_{12}H_{19}NO_4$: C, 59.74; H, 7.94; N, 5.81. Found: C, 59.68; H, 8.13; N, 5.58.

EXAMPLE 5

(+)-2-Aminobicyclo[3.1.0 ]hexane-2,6-dicarboxylic Acid

A solution of the compound prepared as described in Example 4 (0.69 g) in tetrahydrofuran (10 mL) was treated with 1N sodium hydroxide (10 mL), and the resulting mixture vigorously stirred at room temperature. After several days, the title compound was isolated by anion-exchange chromatography (Bio-Rad AG1-X8), eluting with 50% acetic acid/water, to give 0.53 g of the title compound.

FDMS: m/z=186 (M+H).

Optical rotation: $\alpha_D$=21.32° (c=1, 1N HCl).

Analysis calculated for $C_8H_{11}NO_4 \cdot 1.25H_2O$: C, 46.26; H, 6.55; N, 6.74. Found: C, 46.68; H, 6.47; N, 6.49.

EXAMPLE 6

2-Oxobicyclo[3.1.0]hexane-6-carboxylic acid

A mixture of 60 g of (1SR,5RS,6SR) ethyl 2-oxobicyclo[3.1.0]hexane-6-carboxylate and 300 ml of 1N sodium hydroxide was stirred at 25°–30° C. After 2.5 hours, concentrated hydrochloric acid was added to adjust the pH to 0.8–1.2. The resulting solution was extracted with ethyl acetate. The extracts were dried over magnesium sulfate, filtered, and concentrated to give 49.1 g (98%) of the crude material. Recrystallization from 100 ml of ethyl acetate gave the title compound, mp 123.5°–128° C.

FDMS: m/z=140 (M+)

Analysis calculated for $C_7H_8O_3$: C, 60.00; H, 5.75. Found: C, 60.14; H, 5.79.

EXAMPLE 7

2-Oxobicyclo[3.1.0]hexane-6-carboxylic acid salt with (S)-1-phenylethylamine

A solution of 14 g of the compound prepared in Example 6 in 140 ml of 25% ethanol in ethyl acetate was combined with (S)-1-phenylethylamine (1 eq.). After stirring overnight, the precipitated salt was isolated by filtration and dried to give 11.87 g (45.4%) of the desired salt. Conversion of the salt to the partially resolved 2-oxobicyclo[3.1.0]hexane-6-carboxylic acid by the method of Example 8 and analysis indicated that the salt was 68% ee. The enantiomeric excess was determined by conversion to the methyl ester with diazomethane followed by chiral HPLC on a Chiralpak AS column at 40° C. eluted with 10% isopropanol/90% hexane at 1 ml/min with detection at 210 nm.

EXAMPLE 8

(+)-2-Oxobicyclo[3.1.0]hexane-6-carboxylic acid

A mixture of 1.31 g of the product of Example 7 and 10 ml of 1N hydrochloric acid was stirred for 5 minutes and extracted with ethyl acetate. The extracts were dried over sodium sulfate, filtered, and concentrated to give 0.61 g of the title compound, mp 110°–115° C. The product was determined to be 68% ee by chiral HPLC (method of Example 7).

FDMS: m/z=141 (M+H)

Optical Rotation: $\alpha_D$=49.85°

EXAMPLE 9

(−)-2-Spiro-5'-hydantoinbicyclo[3.1.0]hexane-6-carboxylic acid

A solution of the compound prepared as described in Example 8 (68% ee, 1 eq.), potassium cyanide (1.25 eq.), and ammonium carbonate (2.5 eq) were combined and stirred in ethanol/water at 25° C. for 40 hours. The mixture was acidified with 6N hydrochloric acid, concentrated, diluted with water, and filtered to give a 79% yield of a 90:10 mixture of diastereomers, mp 286°–290° C. The diastereomeric mixture was recrystallized from isopropanol/water to give in 48% yield the title compound in 100% diastereomeric and 100% enantiomeric purity (enantiomeric ratio determined by chiral HPLC on a 4.6×150 mm Chiralcel OD-H column, eluted with 15% Isopropanol/85% hexane at 1 ml/min at 40° C. with detection at 220 nm; diastereomeric ration determined by HPLC on a Zorbax SB-phenyl column at 40° C. with elution with 90:10 buffer/acetonitrile eluted at 2 ml/min with detection at 220 nm (buffer=0.1M dibasic sodium phosphate monohydrate adjusted to pH 2.1 with phosphoric acid).

FDMS: m/z=211 (M+H)

Optical Rotation: $\alpha_D$=−25.98°

Analysis calculated for C9H10N2O4: C, 51.43; H, 4.79; N, 13.33. Found: C, 51.38; H, 4.80; N, 13.26.

EXAMPLE 10

Ethyl 2-spiro-5'-hydantoinbicyclo[3.1.0]hexane-6-carboxylate

A mixture of 5.05 g of ethyl 2-oxobicyclo[3.1.0]hexane-6-carboxylate, 2.15 g of potassium cyanide, 5.77 g of ammonium carbonate, 30 ml of 2B-3 ethanol, and 12 ml of water was stirred at 35° C. until the reaction was complete by HPLC. After 15 hours, the reaction mixture was cooled to 0° C. and 33 ml of water was added to the mixture. After 2 hours at 0° C., the precipitate was isolated by filtration and dried to give 5.23 g (73%) of the title compound, mp 217°–220° C.

FDMS: m/z=238.1 (M+)

Analytical calculated for $C_{11}H_{14}N_2O_4$: C, 55.46; H, 5.92; N, 11.76. Found: C, 55.74; H, 5.88; N, 11.50.

EXAMPLE 11

2-Spiro-5'-hydantoinbicyclo[3.1.0]hexane-6-carboxylic acid

A mixture of 16.32 g of the product of Example 10 and 137 ml of 2N NaOH was stirred at 25° C. After 1 hour, concentrated hydrochloric acid was added to adjust the DH to 1.0. The resulting precipitate was isolated by filtration and dried to give 13.70 g (95%) of the title compound, mp 277°–279° C.

FDMS: m/z=210.1 (M+)

Analysis Calculated for $C_9H_{10}N_2O_4$: C, 51.43; H, 4.79; N, 13.33. Found: C, 51.70; H, 4.93; N, 13.43.

EXAMPLE 12

2-Spiro-5'-hydantoinbicyclo[3.1.0]hexane-6-carboxylic acid, (S)-1-phenylethylamine salt A mixture of 1.05 g of the product of Example 11 and 16.6 ml of a 1.6:1 solution of acetone: water was stirred at 25° C. while adding 1.53 g of R-(+)-1-phenylethylamine. The mixture was stirred for 2 hours at room temperature. The crystals were filtered, rinsed with acetone, and dried to give 0.74 g (45%) of the title compound, mp 205°–212° C.

Optical Rotation: $\alpha_D$=−31.88° (c=1, methanol)

EXAMPLE 13

(−)-2-Spiro-5'-hydantoinbicyclo[3.1.0]hexane-6-carboxylic acid

A mixture of 0.74 g of the product of Example 12 and 10 ml of water was stirred at 25° C. while the pH was adjusted from 6.81 to 1.0 using 1N HCl. The reaction mixture was stirred for 1 hour and the product was collected by filtration and dried to give 0.35 g (75%) of the title compound, mp 310° C. (decomp).

FDMS: 210.1 (M+)

Optical Rotation: $\alpha_D = -24.22°$ (c=1, methanol)

Analysis calculated for $C_9H_{10}N_2O_4$: C, 51.43; H, 4.80; N, 13.33. Found: C, 51.67; H, 4.87; N, 13.61.

EXAMPLE 14

(+)-2-Aminobicyclo[3.1.0]hexane-2,6-dicarboxylic Acid

A solution of 184 g of (−)-2-spiro-5'-hydantoinbicyclo[3.1.0]hexane-6-carboxylic acid and 1750 ml of 3N NaOH was heated at reflux until the reaction was complete by HPLC. After 28 hours, the solution was cooled to room temperature and filtered through glass paper to remove trace amounts of insoluble material. The pH of the solution was adjusted to 3.0 using concentrated HCl. The reaction mixture was stirred 1 hour at room temperature and two hours at 0° C. The precipitated product was collected by filtration, washed with 170 ml of cold water and dried to give 152.5 grams (86%) of the title compound.

FDMS: m/z=186.1 (M+1)

Optical rotation: $\alpha_D = 23.18°$ (c=1, 1N HCl)

We claim:

1. A method of protecting a warm blooded mammal from dependence on a benzodiazepine, which comprises administering to a warm blooded mammal in need of protection an effective amount of an agonist which acts at negatively coupled cAMP-linked metabotropic glutamate receptors.

2. A method as claimed in claim 1, in which said benzodiazepine is diazepam.

3. A method as claimed in claim 1, in which said agonist is administered before said benzodiazepine is first administered.

4. A method as claimed in claim 1 in which said agonist is administered after said benzodiazepine has been administered.

5. A method as claimed in claim 1, in which said agonist is administered after said benzodiazepine has been withdrawn.

6. A method as claimed in claim 1, in which said agonist is co-administered with said benzodiazepine.

7. A method as claimed in claim 1, in which said agonist acts selectively at negatively coupled cAMP-linked metabotropic glutamate receptors.

8. A method of protecting a warm blooded mammal from dependence on nicotine, which comprises administering to a warm blooded mammal in need of protection an effective amount of an agonist which acts at negatively coupled cAMP-linked metabotropic glutamate receptors.

9. A method as claimed in claim 8, in which said mammal is ceasing smoking.

10. A method as claimed in claim 8, in which said agonist acts selectively at negatively coupled cAMP-linked metabotropic glutamate receptors.

11. A method of treating a warm blooded mammal for benzodiazepine tolerance, withdrawal or cessation, which comprises administering to a warm blooded mammal in need of treatment an effective amount of an agonist which acts at negatively coupled cAMP-linked metabotropic glutamate receptors.

12. A method as claimed in claim 11, in which the benzodiazepine is diazepam.

13. A method as claimed in claim 11, in which said agonist acts selectively at negatively coupled cAMP-linked metabotropic glutamate receptors.

14. A method of treating a warm blooded mammal for nicotine tolerance, withdrawal or cessation, which comprises administering to a warm blooded mammal in need of treatment an effective amount of an agonist which acts at negatively coupled cAMP-linked metabotropic glutamate receptors.

15. A method as claimed in claim 14, in which said agonist acts selectively at negatively coupled cAMP-linked metabotropic glutamate receptors.

16. A method of treating a warm blooded mammal for smoking cessation, which comprises administering to a warm blooded mammal in need of treatment an effective amount of an agonist which acts at negatively coupled cAMP-linked metabotropic glutamate receptors.

17. A method as claimed in claim 16, in which said agonist acts selectively at negatively coupled cAMP-linked metabotropic glutamate receptors.

18. A method of protecting a warm blooded mammal from dependence on dependence-producing substance, which comprises administering to a warm blooded mammal in need of protection an effective amount of an agonist which acts selectively at negatively coupled cAMP-linked metabotropic glutamate receptors.

19. A method of treating a warm blooded mammal for drug tolerance, withdrawal or cessation, which comprises administering to a warm blooded mammal in need of treatment an effective amount of an agonist which acts selectively at negatively coupled cAMP-linked metabotropic glutamate receptors.

20. A method as claimed in claim 7, in which said agonist is (+)-2-aminobicyclo[3.1.0]hexane-2,6-dicarboxylic acid.

21. A method as claimed in claim 10, in which said agonist is (+)-2-aminobicyclo[3.1.0]hexane-2,6-dicarboxylic acid.

22. A method as claimed in claim 13, in which said agonist is (+)-2-aminobicyclo[3.1.0]hexane-2,6-dicarboxylic acid.

23. A method as claimed in claim 15, in which said agonist is (+)-2-aminobicyclo[3.1.0]hexane-2,6-dicarboxylic acid.

24. A method as claimed in claim 17, in which said agonist is (+)-2-aminobicyclo[3.1.0]hexane-2,6-dicarboxylic acid.

25. A method as claimed in claim 18, in which said agonist is (+)-2-aminobicyclo[3.1.0]hexane-2,6-dicarboxylic acid.

26. A method as claimed in claim 19, in which said agonist is (+)-2-aminobicyclo[3.1.0]hexane-2,6-dicarboxylic acid.

* * * * *

UNITED STATES PATENT AND TRADEMARK OFFICE
CERTIFICATE OF CORRECTION

PATENT NO. : 5,661,184
DATED : August 26, 1997
INVENTOR(S) : David R. Helton, et al.

It is certified that error appears in the above-identified patent and that said Letters Patent is hereby corrected as shown below:

On the title page, item [56], under References Cited:

"WO95/15940 6/1995 WIPO" should read --
WO95/15940

"Canadian Journal of Pharmacology, XIIth International Congress of Pharmacology Abstracts, vol. 72. Supplement 1, issued 24 Jul. 1994. M.E. Fundytus, et al., "Acute ICV Injection of the Metabotropic Glutamate Receptor Agonists trans-ACPD Attenuates Morphine Withdrawal in Rats". P. 349, col. 2. Abstract No. P13.5.18."

Should read --

Canadian Journal of Pharmacology, M.E. Fundytus et al., "Acute ICV Injection of the Metabotropic Glutamate Receptor Agonist trans - ACPD Attenuates Morphine Withdrawal in Rats, July 1994, abstract.

XIIth International Congress of Pharmacology Abstracts, vol. 72, Supplement 1, issued 24 Jul. 1994, M.E.

Signed and Sealed this

Sixteenth Day of February, 1999

Attest:

*Attesting Officer*

*Acting Commissioner of Patents and Trademarks*